United States Patent
Sanchez Jaime (10) Patent No.: US 12,127,970 B2
(45) Date of Patent: Oct. 29, 2024

(54) DEVICE FOR PROTECTING SKIN AND TISSUES FOR AESTHETIC COLD TREATMENTS

(71) Applicant: HIGH TECHNOLOGY PRODUCTS, S.L.U., Barcelona (ES)

(72) Inventor: Jose Antonio Sanchez Jaime, Barcelona (ES)

(73) Assignee: HIGH TECHNOLOGY PRODUCTS, S.L., Barcelona (ES)

(*) Notice: Subject to any disclaimer, the term of this patent is extended or adjusted under 35 U.S.C. 154(b) by 1478 days.

(21) Appl. No.: 16/336,239

(22) PCT Filed: Jan. 19, 2017

(86) PCT No.: PCT/ES2017/070032
§ 371 (c)(1),
(2) Date: Mar. 25, 2019

(87) PCT Pub. No.: WO2018/060533
PCT Pub. Date: Apr. 5, 2018

(65) Prior Publication Data
US 2019/0209259 A1 Jul. 11, 2019

(30) Foreign Application Priority Data
Sep. 28, 2016 (ES) .................. 201631263

(51) Int. Cl.
*A61F 7/10* (2006.01)
*A61F 7/02* (2006.01)

(52) U.S. Cl.
CPC ........ *A61F 7/10* (2013.01); *A61F 2007/0219* (2013.01); *A61F 2007/108* (2013.01)

(58) Field of Classification Search
CPC ..................................................... A61B 90/04
See application file for complete search history.

(56) References Cited

U.S. PATENT DOCUMENTS

2008/0268216 A1* 10/2008 Quincy .................... D06N 3/04
427/407.1

FOREIGN PATENT DOCUMENTS

EP          1157817 A2 * 11/2001    ....... A61F 13/15577

* cited by examiner

*Primary Examiner* — Kaitlyn E Smith
(74) *Attorney, Agent, or Firm* — Stanzione & Associates, PLLC; Patrick Stanzione (57) ABSTRACT

Protective device for the skin and tissues for cold cosmetic treatments including at least a first layer (1) of a cold conducting material, characterized in that it comprises:
at least a second layer (2) on said first layer (1) and joined to it (1), defining some inner surfaces (3) between both layers configuring at least one housing (11), being both layers (1, 2) porous and absorbent, and
at least one cold conducting antifreeze gel (4), scattered in housing (11), on all the inner surfaces (3), said gel (4) having a freezing point below −12° C., and a viscosity between 2000-90000 cPs at 21° C., enough to pass through the pores of layers (1, 2) and to be removed from housing (11).

10 Claims, 7 Drawing Sheets

DEVICE FOR PROTECTING SKIN AND TISSUES FOR AESTHETIC COLD TREATMENTS

CROSS-REFERENCE TO RELATED APPLICATIONS

This application claims the benefit of priority under 35 U.S.C. § 120 to international patent application number PCT/ES2017/070032, filed on Jan. 19, 2017, which claims the benefit of prior patent application number P201631263, filed in Spain on Sep. 28, 2016, the contents of which are incorporated herein in their entirety.

DESCRIPTION

Protective device for skin and tissues for cold cosmetic treatments, of the type comprising at least a first layer, and in that it comprises: at least a second layer on said first layer and joined to it, defining inner surfaces between both layers configuring at least one housing, with both layers being porous and absorbent, and at least one cold conducting antifreeze gel scattered in the housing on all the inner surfaces, said gel (4) having a freezing point below −12° C., and a viscosity between 2000-90000 cPs at 21° C., which is enough to pass through the pores of the layers and to be removed from the housing.

BACKGROUND TO THE INVENTION

Different devices are known in the state of the art which protect the skin from the coldness in cryotherapy treatments and the like.

Thus, Chinese Patent CN102440844 "CLINICAL PROTECTOR" in the name of KAIYAN LIANG, from 2010 is known, which relates to a clinical protector, which belongs to the field of medical apparatus. The clinical protector comprises a circular guide ring, a first vertical groove arranged on the top and a second vertical groove arranged on the bottom of the circular guide ring, at least two horizontal outside deflectors installed in the first vertical groove, at least two horizontal inside deflectors installed in the second vertical groove, a vertical installation deflector at the inner ends portions of the inner horizontal, interior deflectors, a rubber protective pad installed in the vertical deflector, a first separation block and a second spacing block. The invention overcomes the defects of the known and published state of technology, as the size of the clinical protector can be adjusted according to the shape of the coated part, so that this way the clinical protector is joined closely to the protected skin so that at the same time it protects the healthy skin around the affected part of the patient and prevents liquid nitrogen from causing unnecessary damage to the healthy skin. The invention has the advantage of being a simple, low cost structure, comfortable to use, and it largely improves the safety of cryosurgery.

Also, the state of the art includes Patent WO2007127924 "CRYOPROTECTANT FOR USE WITH A TREATMENT DEVICE FOR IMPROVED COOLING OF SUBCUTANEOUS LIPID-RICH CELLS", from 2007, in the name of JUNIPER MEDICAL, INC. which relates to a cryoprotectant for use with a treatment device for the improved removal of heat from the cells rich in subcutaneous lipids of a patient's skin. The cryoprotectant is a liquid, a gel or a paste that does not freeze and which allows a device to be precooled to a temperature below 0° C. while preventing the formation of ice on the device. The cryoprotectant also prevents the device and the actual skin from freezing, and also prevents ice appearing on the skin.

BRIEF DESCRIPTION OF THE INVENTION

The present application comes under the field of devices that are used for cold cosmetic treatments and for the so-called cryotherapy treatments.

The closest document is the cited patent WO2007127924. Thus, it solves the problem of the avoiding the healthy area being exposed to the action of the cooling, therefore preventing it from getting damaged.

For that, a device has been built which is placed between the element issuing the coldness and the patient's skin.

A rigid protector containing a gel which, in turn is inside a cover, is anchored or fixed to said device.

Many problems arise here. On the one hand, due to the fact that it includes anchoring elements, it can only be used for certain heads made by one particular head manufacturer, and not for all.

Also, and along the same lines as above, it can only be used with a head with a certain, specific size, which prevents it from being used with heads with a similar size.

Neither can it be used in heads with suction, since the rigidity of the protector prevents it from being absorbed, and it is even less able to adapt to the suction since it is fixed.

With regard to hygiene, since they are devices that are used with different patients, devices that are in contact with the skin are susceptible to becoming infected with viruses or bacteria, consequently, the safest solution is to clean the product thoroughly or to dispose of it. Even though the closest document includes a cover that could become disposable, the actual protector is not disposed of, and this way the gel can also be contaminated, and that does remain and is used on the next patient. In fact, it is envisaged refilling it, which contradicts the idea of being disposable.

Therefore, the hygiene issue is important, as all the devices need to be disposable to avoid the propagation of skin diseases, if applicable.

The device of this invention is arranged, stretched out, with one of its layers in contact with the patient's skin, the epidermis, in the area that is going to be treated, and the other layer in contact with the cold issuing device or cold means (an ice bag for example, or a head end such as the one described in European Patent EP2687174).

The surface opposite the patient's skin is porous, so that it can transmit the coldness to the skin, and the other surface which is in contact with the head end is also porous to prevent isolating the coldness produced by said head end. The essential aim of the membrane is to protect the dermal tissue, while the coldness or cryotherapy treatments are carried out, and prevent said tissues from possibly freezing.

So, there is an antifreeze gel between the two layers of the device or membrane, so that the gel always impregnates the layers, preventing the skin from being damaged by the ice.

This is aided by the fact that the second layer, the one that is on the patient's skin, is made from a skin protecting material.

This way the cool transmitted by the cooling head, first reaches the antifreeze gel that comes out of the pores, then the first layer of the protector, the antifreeze gel in the housing, the second layer and finally the antifreeze gel that filters through the pores of the second layer that is in contact with the patient's skin.

The protective membrane can have various sizes and different amounts of gel, proportional to said size.

One aim of the double protective membrane is to guarantee the safety of the dermal area treated by the cryotherapy (and the suction), preventing it from freezing.

A second aim of the double protective membrane is to be able to adapt to the contours of the skin thanks to its flexibility.

A third aim is that the actual double membrane adapts to the suction by the head end, while still protects the skin.

In other words, it intensifies and transmits the coldness in the area due to the antifreeze gel, and on the other hand it prevents burns that could occur if there were no gel between the cold means and the patient's skin.

An aim of this invention is a protective device for the skin and tissues in cold cosmetic treatments, of the type comprising at least a layer, characterized in that it comprises: at least a second layer on said first layer and joined to it, defining inner surfaces between both layers configuring at least one housing, with both layers being porous and absorbent, and at least one cold conducting antifreeze gel, scattered in the housing, on all the inner surfaces, with a freezing point below −12° C., and with a viscosity of between 2000 and 90000 cPs at 21° C., which is sufficient for passing through the pores in the layers and coming out of the housing.

BRIEF DESCRIPTION OF THE DRAWINGS

In order to facilitate the explanation, this specification is accompanied by seven sheets of drawings representing a practical embodiment thereof, which is provided as a non-limiting example of the scope of this invention.

SPECIFIC EMBODIMENT OF THE INVENTION

Figure 1:
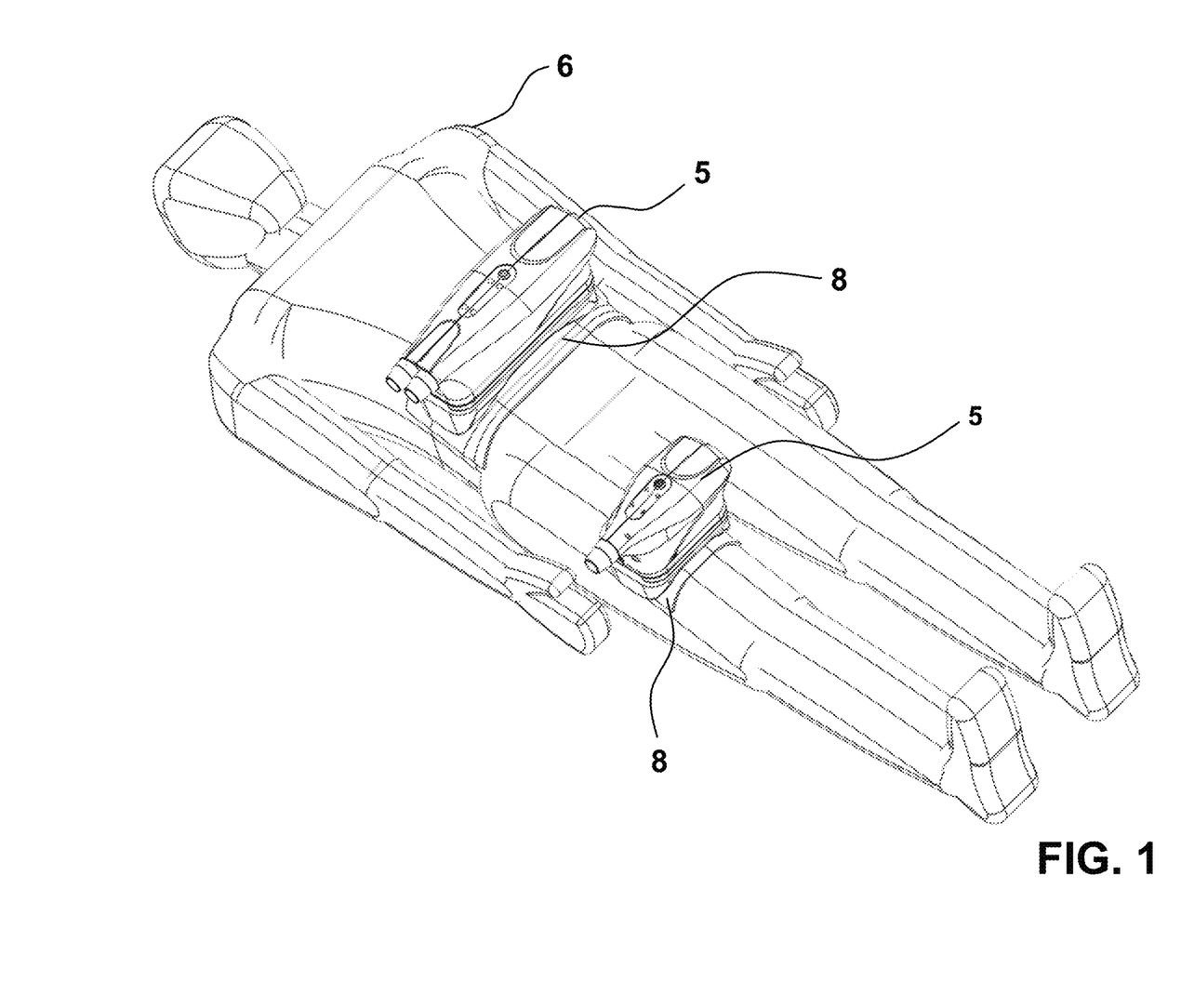
FIG. 1 is a general view of cold heads with the device of this invention.

So, FIG. 1 illustrates a patient 6 on which devices 8 of this invention are placed and some heads 5 are placed on said devices 8.

Figure 2:
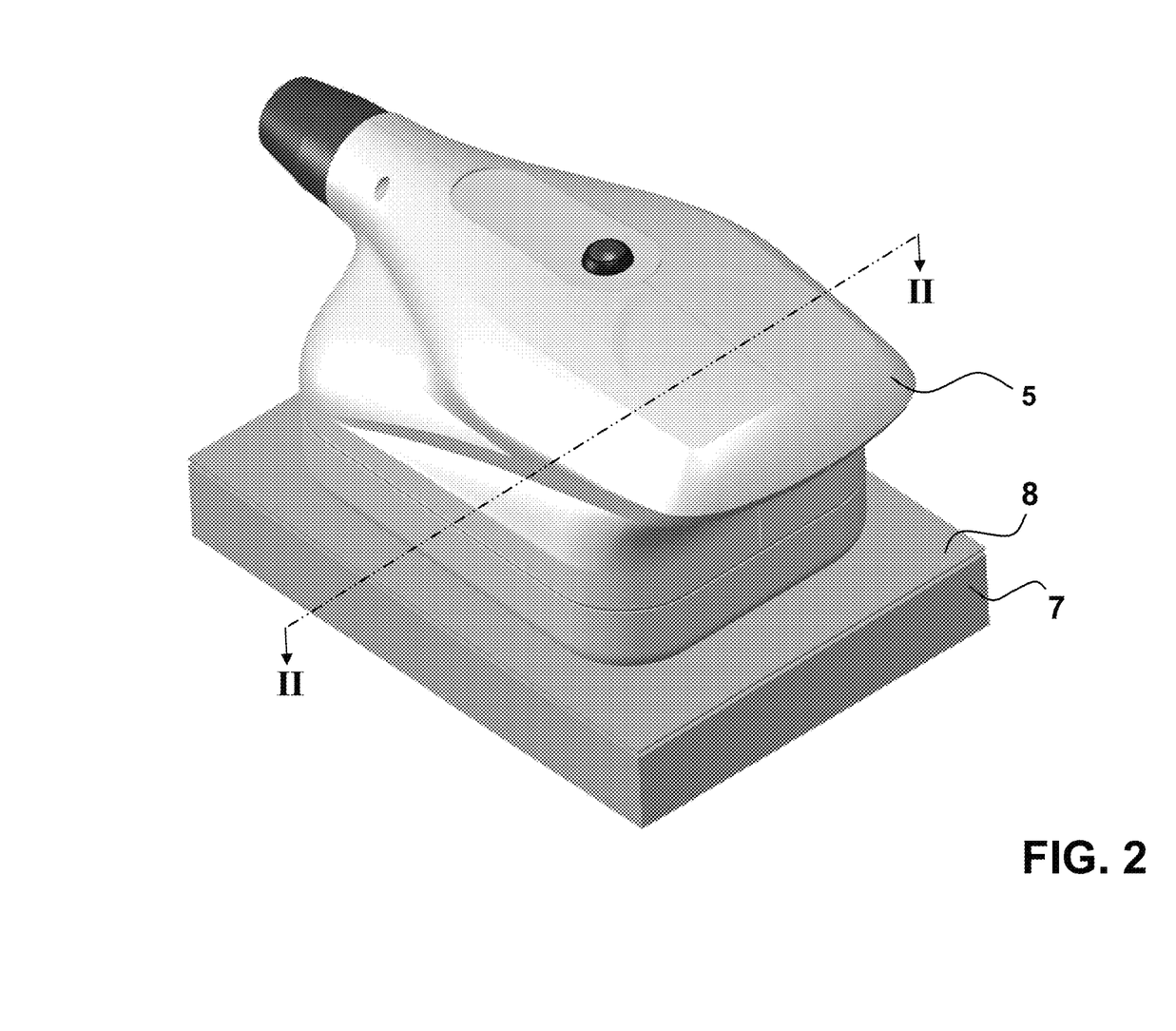
FIG. 2 is a view of the head end with the device and the skin.

FIG. 2 represents the head 5, device 8 and the patient's skin 7.

Figure 3:
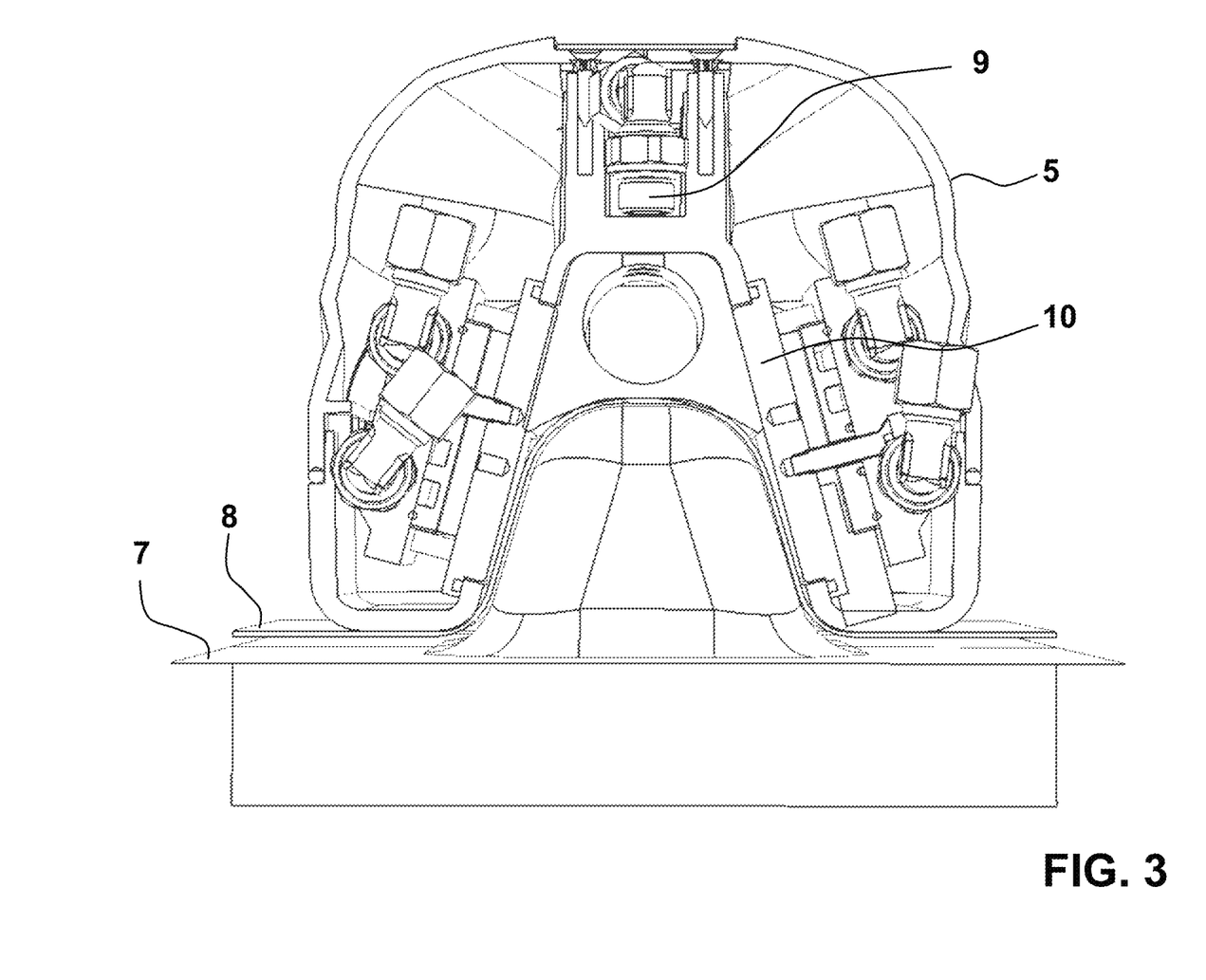
FIG. 3 is a sectional view of FIG. 2, along the line III-III, when the head end is cooling and applying suction to the device and skin.

FIG. 3 shows the head with the suction means 9, cold means 10, device 8 and the patient's skin 7.

Figure 4:
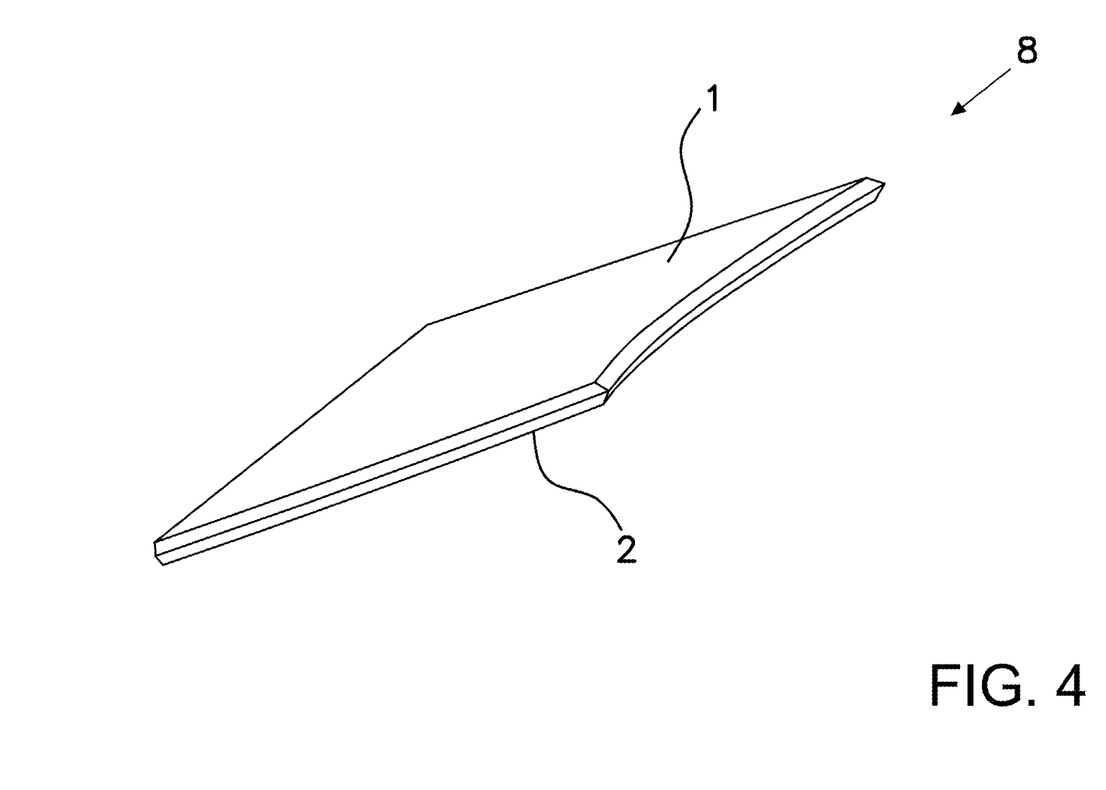
FIG. 4 is a side perspective view of the device.
Figure 5:
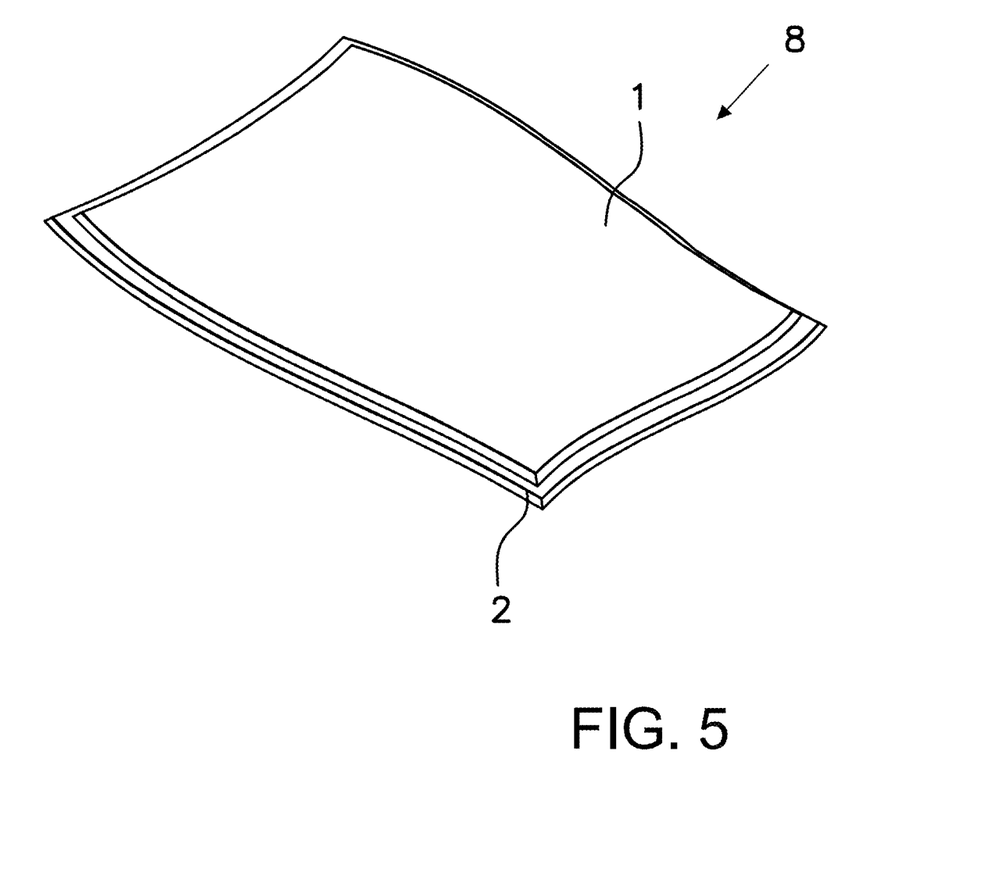
FIG. 5 is a perspective view of another embodiment of the device.
Figure 6:
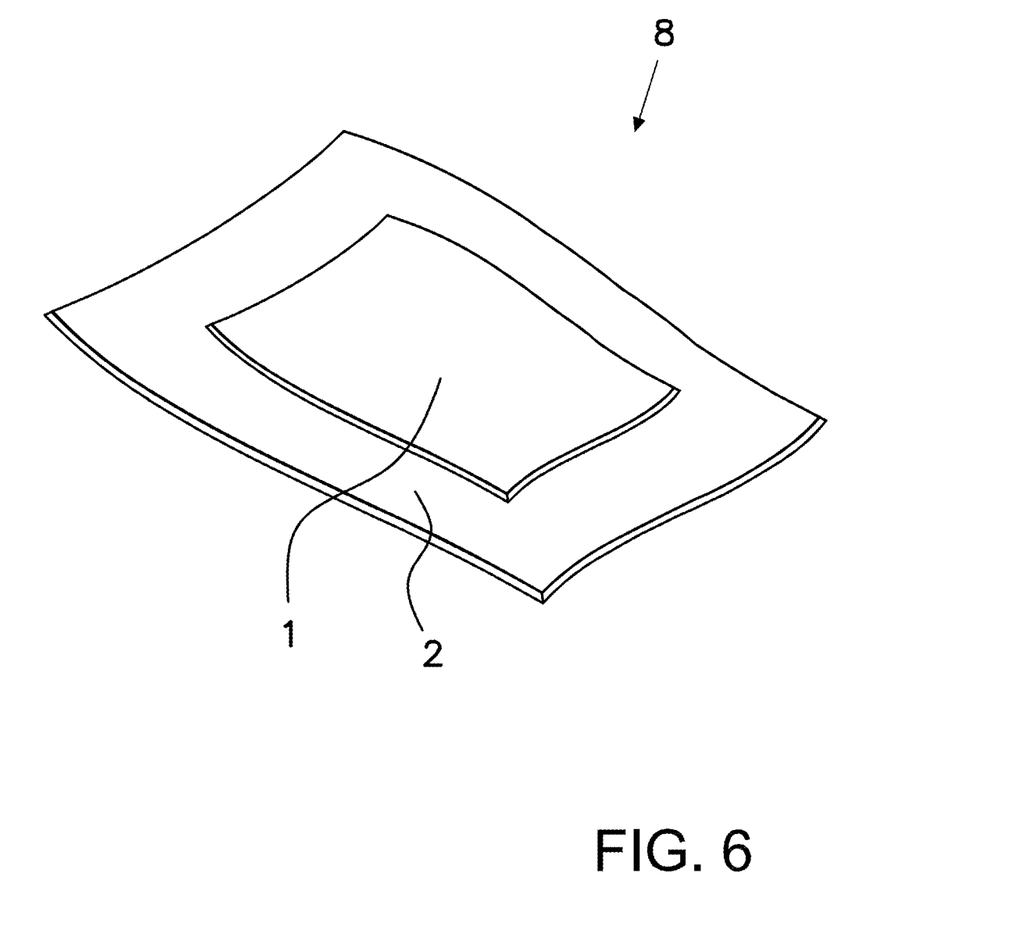
FIG. 6 is a perspective view of another embodiment of the device.

FIGS. 4, 5 and 6 show the device with its first layer 1 and its second layer 2.

Figure 7:
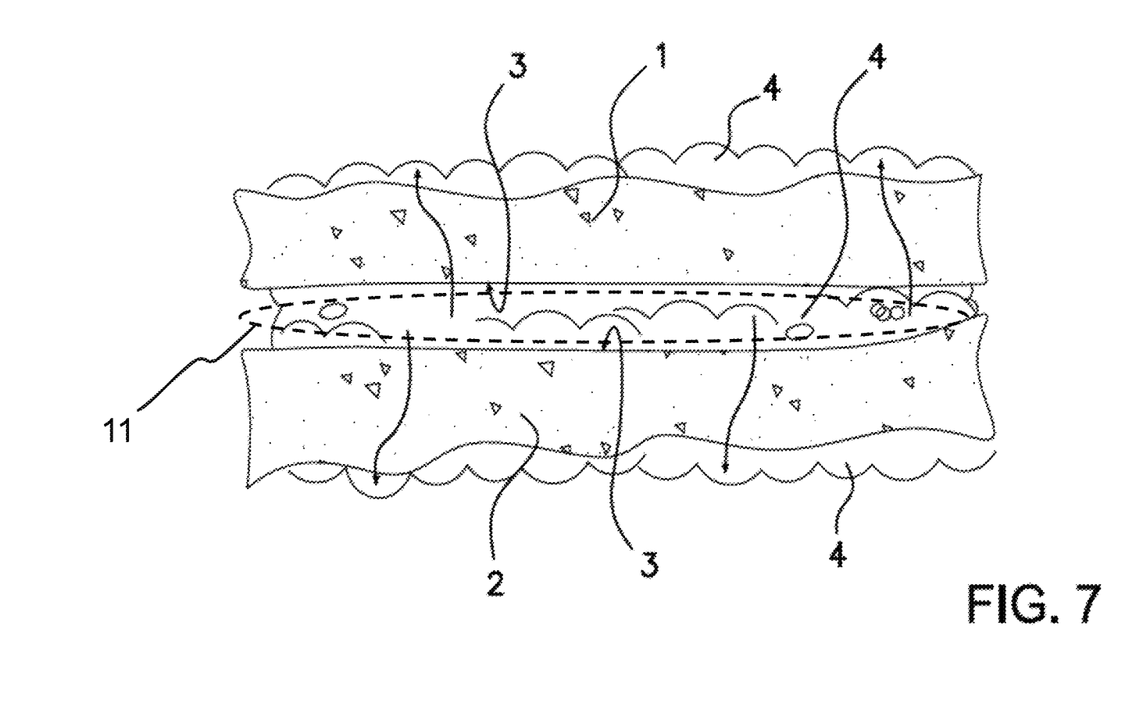
FIG. 7 is a detail of how the device works.

Lastly, FIG. 7 shows device 8, first layer 1, second layer 2, inner surfaces 3, a housing 11, and an antifreeze gel 4.

Firstly, in FIGS. 4, 5 and 6, antifreeze gel 4 is shown in the drawings. Usually, since the first layer 1 is joined to the second layer 2 around its perimeter, it is not possible to see antifreeze gel 4 from the outside, unless it comes out of the pores. These figures show this effect to help the reader understand the position of antifreeze gel 4 inside, even though in many of the embodiments you could not see it from the outside.

So, in a specific embodiment, device 8, the aim of this invention, comprises at least a first layer 1 of porous material, that protects the patient's skin, and in principle in this embodiment one single layer is envisaged, but one or several additional layers of hypoallergenic material, etc. could be added.

The material of first layer 1 has to be porous to allow antifreeze gel 4, the cold conductor, to transmit the coldness to the antifreeze gel 4 that is inside the housing 11.

This way, the coldness, through antifreeze gel 4, ends up reaching the patient.

It comprises at least a second layer 2 of porous material on said first layer 1 and joined to it 1, forming a whole, defining some inner surfaces 3 between both layers, that is, surfaces where both layers would touch if gel 4 were not inside them. Between both inner surfaces a housing 11 is formed for containing antifreeze gel 4.

As in the first layer 1, in this embodiment second layer 2 only has one layer, although it could have more than one if additional layers were arranged with hypoallergenic materials, creams, etc.

It also comprises at least one antifreeze gel 4, scattered on inner surfaces 3, in housing 11, with a freezing point below −12° C., leaving both layers 1, 2 joined, forming a single unit.

The temperature of the freezing point of antifreeze gel 4 must be as minimum −12° C., since even when the working temperature is usually −8° C., there are times when due to the type of treatment to be applied, the temperature must be −12° C. and even tests have been conducted where it has reached down to −20° C.

Said layer must be porous in order to be able to transmit the coldness to the patient's skin 7 through antifreeze gel 4.

In other words, the antifreeze gel 4, which is in contact with the coldness transmitted by cold means 10 of head 5, transmits the coldness to the antifreeze gel 4 in the housing 11, through the pores in the first layer, and the coldness that the antifreeze gel 4 in housing 11 has received, in turn transmits this coldness to the antifreeze gel 4 in contact with the patient's skin through the pores of the second layer 2 (FIG. 7).

Regarding the antifreeze gel 4, this must have sufficient viscosity, which it has been calculated should be between 2000 and 90000 centipoises (cPs) at 21° C., Rotor 3 at 3 RPM, to pass through the pores in layers 1, 2 and come out of the housing 11. An intermediate standard viscosity could be between 35000 and 38000 cPs.

An example of the formula of antifreeze gel 4 could be:
Solvent—for example water, between 25 and 50%,
Solvent-Wetting agent—for example glycerine, between 50 and 75%,
Viscosity controllers (for example cellulose) between 0.1 and 2.0% and,
Preservatives (for example, magnesium nitrate, magnesium chlorate, etc., between 0.01 and 0.1%).

Also, said antifreeze gel 4 in the example must have at 21° C.:
a pH between 5.0 and 7.0 pH units, and
a density between 0.990 and 1.200 g/ml
The visual perception must be stable in all assays.

The ranges indicated depend on the porosity of the first layer 1 and the second layer 2, is they are more porous, i.e. they let more antifreeze gel 4 pass through, viscosity will reduce so that it flows more slowly between the pores in layers 1, 2, approaching 90000 cPs, on the other hand if layers 1,2 are less porous, the viscosity of the antifreeze gel 4 will increase in order to increase the flow of antifreeze gel 4 between the pores of layers 1,2, approaching 2000 cPs.

In order to increase the efficiency of antifreeze gel 4, it has been considered to distribute said antifreeze gel uniformly over all the inner surfaces. This is done to avoid risks of burns in the event that there was a part of device 8 without gel and it was being suctioned and cooled by head end 5.

If there were a part of device 8 that were opposite a part of the patient's skin without antifreeze gel 4, ice would be produced and the skin would consequently be burned.

Therefore, if there were none of said antifreeze gel 4 in a part of device 8, it would allow the coldness and the suction to be felt directly against the patient's skin 7, causing damage and burns on the patient's skin 7.

It can be arranged that in device 8 first layer 1 and second layer 2 are the same size, as appears in FIG. 4. This is done because it is one of the easiest ways to manufacture it, in terms of manufacturing.

It would also be possible that first layer 1 and second layer 2 are different sizes, preferably that the smaller size layer is in the centre of the larger layer, and this is the case illustrated in FIGS. 5 and 6.

Preferably the smallest is first layer 1, and it must be large enough to cover the whole inside of head 5 when it suctions, this way, as there would be the antifreeze gel 4 covering the whole of the area of said first layer 1 on the inner surfaces, there is no risk that there are areas of the patient's skin 7 where coldness and suction are applied and which do not have any antifreeze gel 4.

Optionally, layers 1, 2 are joined together either by, but not limited to sewing, thermosealing or sticking.

Out of the porous materials that can be used to make the layers 1, 2, cellulose could be used. The grammage of cellulose could be between 10 and 200 g/cm$^3$.

Optionally, layers 1, 2 could have a different grammage, since interests the greater grammage in the first layer 1 which is the one that experiences the tension from the suction means 9, where have been envisaged that their fibres can withstand pressures up to 500 mbar without breaking.

In terms of manufacturing, it could be interesting that the second layer 2 had the same grammage as the first layer 1, as this way the whole of device 8 could be manufactured with one single piece of cellulose.

When a cryotherapy treatment is going to be applied to a patient 6, a device 8 will be placed on the patient's skin 7.

The second layer 2 would be on the patient's skin 7 and the first layer 1 would be opposite head 5 (as an example, the one described in EP2687174 is used, in the name of the same applicant).

Then on first layer 1 there would be placed the opening of head 5 and suction means 9 and cold means 10 would be started up.

This would lead to a situation like the one in FIG. 3, where a part of the patient's skin is absorbed by suction means 9, but leaving device 8 between them, that protects the patient's skin 7 mainly from the action of the cold means, preventing ice from forming on the patient's skin.

This way the coldness can penetrate under the patient's skin 7, transmitted by antifreeze gel 4, through the porosity of the second layer 2, but on the other hand the antifreeze gel 4 prevents ice forming on the patient's skin 7 without causing injuries and preventing injuries from burns.

The aim of this invention is to guarantee the safety of the patient's skin 7 treated by cryotherapy and suction, while also stopping the skin from freezing.

This invention describes a new protective device of the skin and tissues for cold cosmetic treatments. The examples mentioned herein do not limit this invention, which therefore could have various applications and/or adaptations, all within the scope of the following claims.

The invention claimed is:

1. A protective device for the skin and tissues for cold cosmetic treatments, the protective device comprising:
    at least one first porous and absorbent layer including an inner surface an outer surface and peripheral ends thereof;
    at least one second porous and absorbent layer including an inner surface, an outer surface and peripheral ends thereof, the periphera ends thereof being connected to the peripheral ends of the at least one first porous and absorbent layer such that the inner surface of the at least one first porous and absorbent layer is seperated from but faces the inner surface of the at least one second porous and absorbent layer;
    a housing formed between the at least one first porous and absorbent layer and the at least one second porous and absorbent layer, the housing configured to store a supply of cold conducting antifreeze gel therein to be distributed therefrom through both the at least one first porous and absorbent layer and the at least one second porous and absorbent layer, and
    a cold conducting antifreeze gel stored within the housing the cold conducting antifreeze gel having a freezing point below −12° C. and a viscosity between 2000-90000 cPs at 21° C. sufficient to pass out of the housing and through the pores of the at least one first porous and absorbent layer to the outer surface thereof to conduct coldness applied by a cold head to the outer surface of the at least one firs porous and absorbent layer through the at least one first porous and absorbent layer and to pass out of the housing and through the pores of the at least one second porous and absorbent layer to the outer surface thereof to protect dermal tissue which comes in contact therewith from freezing.

2. The device according to claim 1, wherein the viscosity of the antifreeze gel is between 35000 and 38000 cPs at 21° C.

3. The device according to claim 1, wherein the at least one first porous and absorbent layer and the at least one second porous and absorbent layer have the same size.

4. The device according to claim 1, wherein the at least one first porous and absorbent layer and the at least one second porous and absorbent layer have different sizes.

5. The device according to claim 4, wherein the smaller of the at least one first porous and absorbent layer and the at least one second porous and absorbent layer is placed in the centre of the larger layer.

6. The device according to claim 1, wherein the at least one first and second porous and absorbent layers are joined together by sewing, thermosealing or sticking.

7. The device according to claim 1, wherein the material of the at least one first and second porous and absorbent layers is formed of a cellulose.

8. The device according to claim 7, wherein the grammage of the cellulose is between 10 and 200 g/cm$^3$.

9. The device according to claim 7, wherein the at least one first and second porous and absorbent layers have a different grammage.

10. The device according to claim 7, wherein th at least one first and second porous and absorbent layers have the same grammage.

* * * * *